United States Patent
Vijfvinkel

[19]

[11] Patent Number: 5,843,111
[45] Date of Patent: *Dec. 1, 1998

[54] VITREOUS REMOVING APPARATUS

[75] Inventor: Gerrit Jan Vijfvinkel, Geervliet, Netherlands

[73] Assignee: Ophthalmic Research Center International bv, Geervliet, Netherlands

[*] Notice: The term of this patent shall not extend beyond the expiration date of Pat. No. 5,630,827.

[21] Appl. No.: 858,383

[22] Filed: May 19, 1997

Related U.S. Application Data

[63] Continuation-in-part of Ser. No. 492,421, Jun. 19, 1995, Pat. No. 5,630,827.

[51] Int. Cl.$^6$ .................................................... A61B 17/32
[52] U.S. Cl. ......................... 606/171; 606/170; 606/167; 604/22
[58] Field of Search ...................................... 606/171, 170, 606/167, 174, 180, 166; 604/22

[56] References Cited

U.S. PATENT DOCUMENTS

| | | | |
|---|---|---|---|
| 3,815,604 | 6/1974 | O'Malley et al. ...................... | 128/305 |
| 4,011,869 | 3/1977 | Seiler, Jr. ............................... | 128/276 |
| 4,111,207 | 9/1978 | Seiler, Jr. ............................... | 606/171 |
| 4,513,745 | 4/1985 | Amoils .................................. | 606/171 |
| 4,589,414 | 5/1986 | Yoshida et al. ........................ | 606/171 |
| 4,662,869 | 5/1987 | Wright .................................. | 604/22 |
| 4,819,635 | 4/1989 | Shapiro ................................. | 128/305 |
| 4,867,157 | 9/1989 | McGurk-Burleson et al. ........ | 128/305 |
| 5,074,841 | 12/1991 | Ademovic et al. ..................... | 604/72 |
| 5,106,364 | 4/1992 | Hayafuji et al. ....................... | 606/171 |
| 5,474,532 | 12/1995 | Steppe .................................. | 604/22 |

*Primary Examiner*—Michael Buiz
*Assistant Examiner*—Daphna Shai
*Attorney, Agent, or Firm*—Hamilton, Brook, Smith & Reynolds, P.C.

[57] ABSTRACT

A surgical instrument provides improved precision and performance for use in highly intricate surgeries such as vitrectomy which frequently involves removing dense vitreous base firmly adherent to the retinal surface. The instrument includes two concentric tubes, an outer tube having ports near the closed end, and a slidable inner tube which fits snugly inside the outer tube. The inner tube includes a sharp cutting edge formed on one end that slides back and forth across the ports to cut vitreous, and an axial passage to pass the cut portions of vitreous. Such a surgical instrument maintains highly effective and accurate cutting member for removing vitreous without cutting into the retina.

15 Claims, 6 Drawing Sheets

5,843,111

VITREOUS REMOVING APPARATUS

RELATED APPLICATIONS

This application is a Continuation-in-Part of application Ser. No. 08/492,421 filed Jun. 19, 1995 U.S. Pat. No. 5,630,827, which is incorporated herein by reference in its entirety.

BACKGROUND OF THE INVENTION

This invention generally relates to a surgical instrument for cutting and removing biological tissue. In particular, the present invention is effective for intraocular surgeries, such as vitrectomy, requiring removal of vitreous or pathologic membranes from the interior of an eye. The vitreous humor fills a large portion of the eye interior behind the lens. It is relatively tough tissue composed of rather complex substance including long protein molecules joined by patches of secondary protein molecules. Typically, a vitrectomy involves removing vitreous in bulk and simultaneously filling the void area with saline. Such a surgery further involves precision removal of vitreous base aligned to the retinal surface.

The intricate procedures of a vitrectomy demand high precision tools that are sufficiently small to enable surgical maneuvering within the interior of a human eye Among the instruments used in intraocular surgeries, those employing a small outer tube with an opening near one end and an inner member providing a cutting means have been in use for some time. These instruments have shown varying effectiveness for cutting and removing vitreous depending on the degree of required surgical precision. In particular, such instruments have operated reasonably well for removing bulk vitreous in the core of vitreous humor where the precision requirement is less critical. However these instruments suffer from lack of heightened precision and performance, for example, for removing denser vitreous base which is more firmly adherent to the retinal surface. As a result, such an instrument tends to cut away the healthy retinal tissue along with vitreous, possibly causing hemorrhage and damage to the retina.

Consequently, a need exists for a high precision instrument suitable for an intraocular surgery, such as vitrectomy, which provides greater precision and safety for removing vitreous without compromising performance. It is further desired that such an instrument provide a means for treating and removing vitreous base near the retinal surface without damaging the healthy tissues of the retina.

SUMMARY OF THE INVENTION

The present invention relates to instruments for use in intraocular surgeries such as vitrectomy. Surgical instruments made according to the present invention overcome lack of precision and safety, often associated with similar instruments of the prior art, without compromising performance. In particular, an instrument in accordance with the present invention is effective for removing vitreous base aligned to the retinal surface.

The present invention generally comprises two small concentric tubes, an outer tube having a closed distal end and an open proximal end, a port near its closed end to draw vitreous, and a slidable inner tube having a sharp edge on one end to cut vitreous. The closed end or the tip of the outer tube forms a smooth, flat surface. The inner tube is coupled to a suction system which provides aspiration to collect cut portions of vitreous. The tubes are sufficiently small so that they can be inserted into an eye to reach the retina through a small incision near the iris. The flat surface on the closed end of the outer tube can then be moved across the retinal surface, effecting a shaving action to remove portions of vitreous base.

In a preferred embodiment, the present invention includes a small outer tube with a closed end having multiple ports near the closed end, and a slidable inner tube, concentric with the outer tube, which fits snugly inside the outer tube. The inner tube includes a sharp cutting edge formed on the distal end that slides back and forth across the ports to cut vitreous, and an axial passage to pass the cut portions of vitreous to the suction system. Preferably, the diameter of the outer tube is about 0.9 mm or less. The preferred ports are slits, each having an opening width of about 0.1 mm or less, and the distal slit is formed within about 0.5 mm from the closed end. The inner tube is coupled to a driver which drives the inner tube back and forth at a variable rate. The inner tube is also coupled to a vacuum which provides aspiration to draw in vitreous through the outer tube ports and to pass the cut portions of vitreous through the axial passage of the inner tube. The ports, each having relatively small opening, promote precision, while multiple ports allow sufficient volume to flow.

In the preferred embodiment, the slits are angled within the range of 5 to about 10 degrees away from or toward the closed end from a plane which is perpendicular to the longitudinal axis of the outer tube, and each has an opening width of about 0.1 mm or less. Each slit extends about half the diameter of the outer tube and is spaced at 0.25 mm center-to-center from the other. Again, such port configuration adds improved precision particularly for shaving dense vitreous formed on the retinal surface. The angled slits provide improved cutting angle and accuracy so that the possibility of cutting into healthy retinal tissue may be virtually eliminated. On the other hand, the instrument of the present invention may provide improved precision for removing malignant or undesired retinal tissue as required in various types of intraocular surgeries. In particular, the present device having the preferred configuration may provide improved precision for cutting retinal edge resulting from a retinotomy, and retinal surface which has been previously treated with diathermy to prevent hemorrhage. In another embodiment, the ports may form circular holes of about 0.1 mm in diameter.

In the preferred embodiment, the inner tube comprises a portion near the sharp edge forming one diameter and the remaining portion forming a smaller diameter. The larger portion begins at the sharp edge and axially extends for about 1.2 mm which, when the inner tube is fully slid inside the outer tube, approximately covers the ports. The diameter of the larger portion is essentially equal to the inner diameter of the outer tube so that the outer surface of such portion and the inner surface of the outer tube form a surface to surface contact. The remaining portion of the inner tube is slightly smaller to allow a small gap between the outer surface of such portion and the inner surface of the outer tube. Restricting contact area between the tubes minimizes friction while maintaining a tight fit near the ports for effective cutting operation. Further, as to the area in contact, the interior of the outer tube and the exterior of the inner tube are manually polished to further reduce friction.

In accordance with a further inventive concept, the apparatus has plural slits along its distal length and a selective drive mechanism reciprocates the inner tube through different selected stroke lengths past different sets of slits. In accordance with yet another inventive concept, plural slits vary in dimensions from a lesser slit area at the distal end. Preferably, at least one slit is deeper than the most distal slit and wider than the most distal slit.

The above and other features of the invention including various novel details of construction and combinations of parts will now be more particularly described with reference to the accompanying drawings and pointed out in the claims. It will be understood that the particular devices and methods embodying the invention are shown by way of illustration only and not as limitations of the invention. The principles and features of this invention may be employed in varied and numerous embodiments without departing from the scope of the invention.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF A PREFERRED EMBODIMENT

Figure 1:
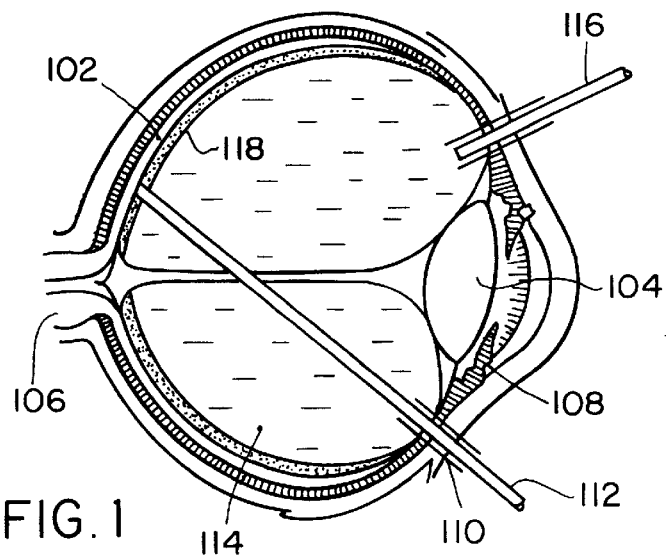
FIG. 1 is a graphical illustration of an intraocular surgery involving vitrectomy.

Referring now to the drawings, FIG. 1 is a general illustration of surgery involving vitrectomy of a human eye. Retina 102 forms the sensory membrane that lines the eye. It receives the image formed by the lens 104 and is the immediate instrument of vision connected with the brain by the optic nerve 106. In an intraocular surgery involving vitrectomy, a small incision 110 is made near the iris 108 to access a cutting instrument 112 into the vitreous humor 114. The cutting instrument then operates to remove vitreous therein while another instrument 116 supplies saline to replenish spaces vacated by the removed vitreous. A layer of tissue 118 formed on the retinal surface represents vitreous base which is a denser tissue more firmly adherent to the retina. Typically, two different types of cutting instruments may be used to perform vitrectomy. The first of these would be a conventional instrument used to remove bulk of vitreous humor 114. The second instrument, such as the one shown at 112, would be used for removing vitreous base which requires greater precision and accuracy.

Figure 2:
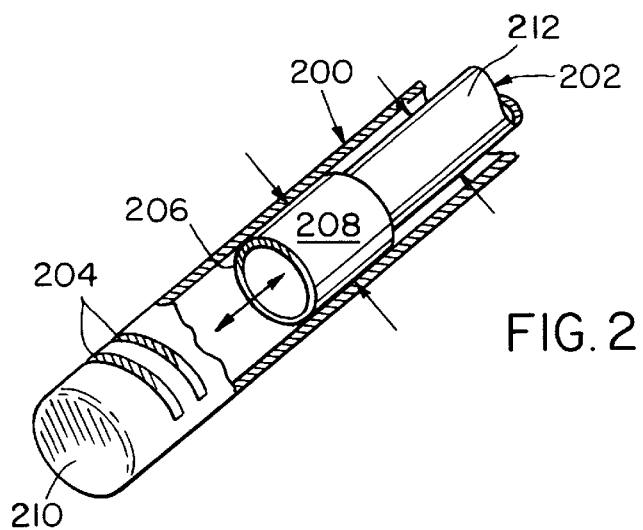
FIG. 2 is a perspective view, partially broken away, of one embodiment of a vitreous removing apparatus according to the present invention.

FIG. 2 is a graphical representation of a preferred embodiment of vitreous removing apparatus according to the present invention. The device, as shown in the cut-away view of FIG. 2, comprises an outer tube 200 and a slidable inner tube 202. The outer tube has a closed-end 210 forming a flat smooth surface and an opposite end which is left open. The outer tube provides ports 204 in the form of slits near the closed end. The inner tube having both ends open provides a sharp cutting edge 206 on one end. In the preferred embodiment, the inner tube consists of a portion 208 having a larger diameter and the remaining portion 212 having a slightly smaller diameter. The larger portion, when the inner tube is fully closed, approximately covers the ports of the outer tube. The diameter of the larger portion is approximately equal to the inner diameter of the outer tube so that the sharp edge crosses the ports tightly when the inner tube is caused to be moved back and forth. The diameter of the remaining portion of the inner tube is smaller than the inner diameter of the outer tube so that no friction exists between the tubes for this portion. As a result, the overall friction between the tubes, when the inner tube is caused to be slid back and forth across the ports, is greatly reduced.

Figure 3:
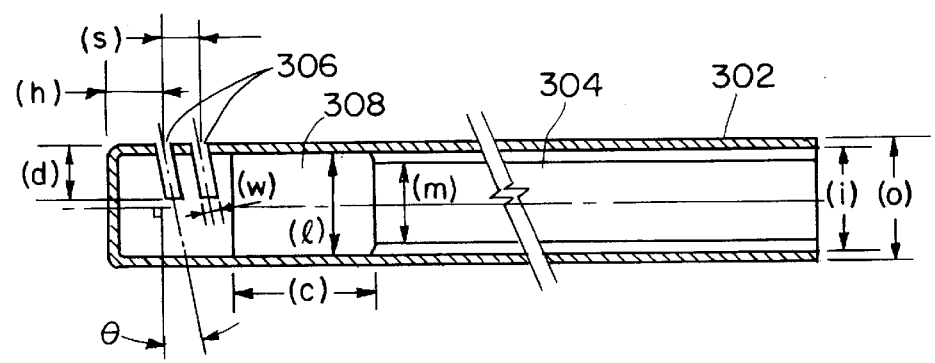
FIG. 3 is a longitudinal view of the apparatus of FIG. 2.

FIG. 3 is a cross-sectional view along the longitudinal axis of the two concentric tubes of the preferred embodiment as described in FIG. 2. The various dimensions of this instrument are particularly shaped and optimized to satisfy the level of precision and performance suitable for a vitrectomy involving the removal of a vitreous base. Each of these dimensions are configured to comply with certain physical requirements such as the aspiration force or the depth of a vitreous base. In this embodiment, the outer tube 302 provides two slits 306, each having width (w) of about 0.1 mm or less, which are spaced so that a center-to-center separation (s) of about 0.25 mm is formed. The device maintains a height (h) of about 0.45 mm between the closed end of the outer tube and the ports. The slits are identically slanted to form an angle (theta) of about 5 degrees from the longitudinal axis and have identical depths (d) which extend about half the diameter of the outer tube. The outer tube 302 has an outer diameter (o) of about 0.9 mm and an inner diameter (i) of about 0.7 mm. The larger portion of the inner tube 308 has an outer diameter (l) of about 0.7 mm, and the remaining smaller portion 304 has an outer diameter (m) of about 0.64 mm.

Figure 9:
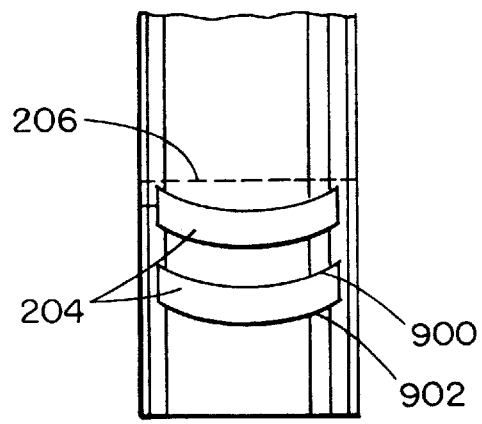
FIG. 9 is a front view of the slits of the vitreous removing apparatus.

FIG. 9 illustrates the slits from the top relative to FIG. 3. It can be seen that each slit is of substantially uniform width between proximal and distal edges 900 and 902 respectively. Those edges extend through a center region between edge ends with the slits being angled such that each end of an edge 900, 902 is proximal relative to the center of the edge. It can be seen that the cutting edge 206 first engages the drawn in vitreous at the outer ends of the slits and cuts toward the center of the slit in a scissor like action against the distal edge 902.

Figure 4:
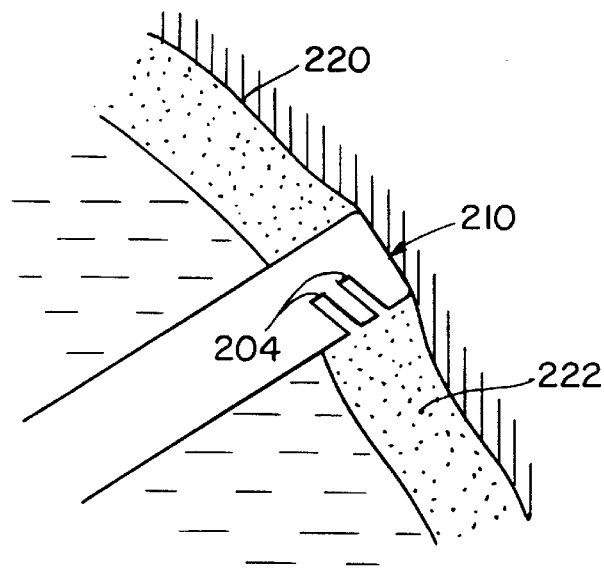
FIG. 4 illustrates precision shaving of vitreous base using a vitreous removing apparatus according to the present invention.

FIG. 4 shows the flat surface of the closed end 210 of the vitreous removing apparatus of FIG. 2 coming in close contact with the retinal surface 220 below a layer of vitreous base 222. Here the device performs what can be described as a "shaving" operation to remove the layer of vitreous base 222. As the device is moved along the retina surface, it draws in the vitreous tissue through its open slits 204, and the sharp edge moving back and forth across the slits severs vitreous. The cut portions of vitreous are then passed through the open end of the inner tube.

Figure 10:
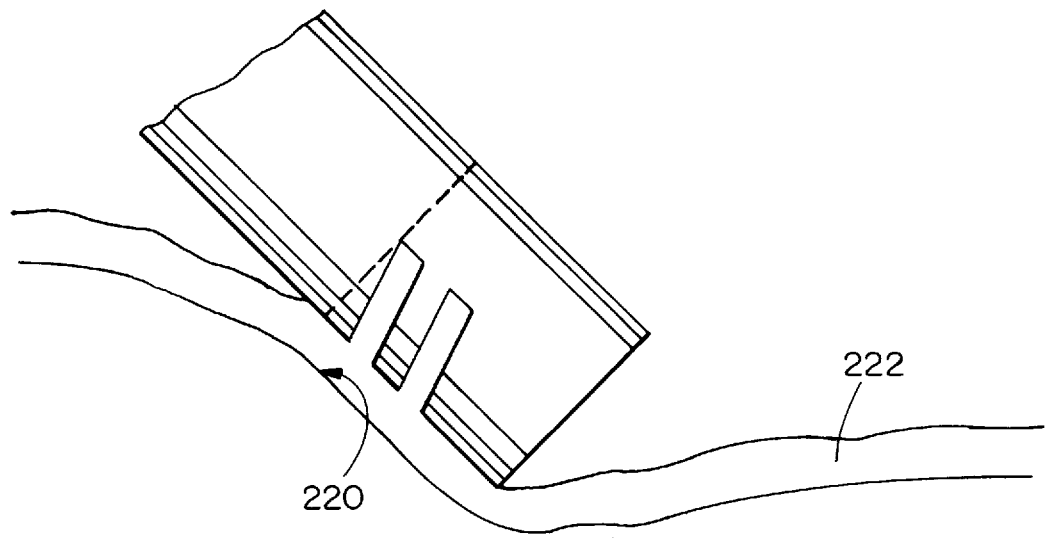
FIG. 10 shows an alternative shaving action of the apparatus.

FIG. 10 illustrates an alternative shaving action of the device with the slits being drawn along the vitreous base 222.

Figure 5:
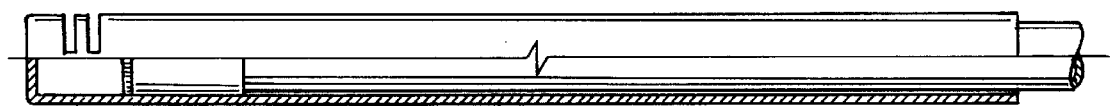
FIG. 5 is another embodiment of the present invention comprising multiple ports.
Figure 6:
FIG. 6 is yet another embodiment of the present invention comprising multiple ports.

FIGS. 5 and 6 show a set of other embodiments according to the present invention which features relatively the same outer and inner tube structures, but has varying port formations. FIG. 5, for example, comprises outer-tube slits that are perpendicular to the longitudinal axis. This embodiment is otherwise identical to that illustrated in FIG. 3. The embodiment in FIG. 6 provides multiple ports made up of small circles each having a diameter of about 0.1 mm. Each of these embodiments includes an inner tube having a sharp cutting edge on one end, and such inner tube forming a thinner-diameter (no-friction) portion and a larger-diameter portion extending from the sharp cutting edge as previously described.

Figure 7:
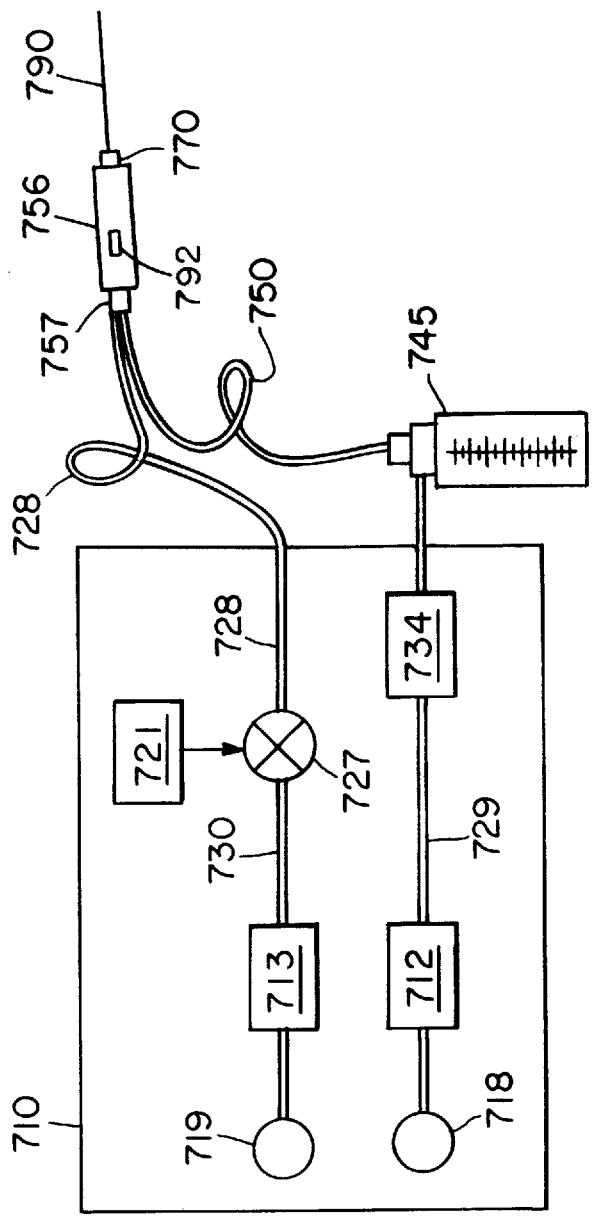
FIG. 7 is a schematic of the surgical apparatus for intraocular surgery including a preferred embodiment of the present invention.

FIG. 7 is a schematic of a surgical apparatus which includes the present invention. A main control unit 710 houses various devices including 2 motors 718, 719 which are mechanically connected to a vacuum pump 713 and an air pressure pump 712. A clock circuit 721 generates output pulses to rotate a pressure control valve 727. The valve 727 is actuated to connect the pressure output line 728 to the pressure line 730. The vacuum line 729 is coupled to a vacuum control device 734. The vacuum control device 734 is further coupled to a measuring cylinder 745 for containing vitreous or other material removed from the eye of the patient.

As described in FIG. 2, the vitreous removing device 790 comprises an outer tube 200 having multiple ports 204 near its closed end and slidable inner tube 202 having a sharp cutting edge 206. The device 790 is attached to one end of a handle 756 through a coupling 770. The handle 756 houses a spring loaded piston to drive the inner tube 202 of the vitreous removing device 790. The handle 756 further provides a tubular projection 757 on the opposite end for receiving both the pressure output line 728 and a flexible tube 750 which connects to the measuring cylinder 745. Vacuum is applied through the flexible tube 750 to aspirate cut vitreous. Similarly, air pressure pulses are applied through the pressure output line 728 to drive the inner tube 202.

Figure 8:
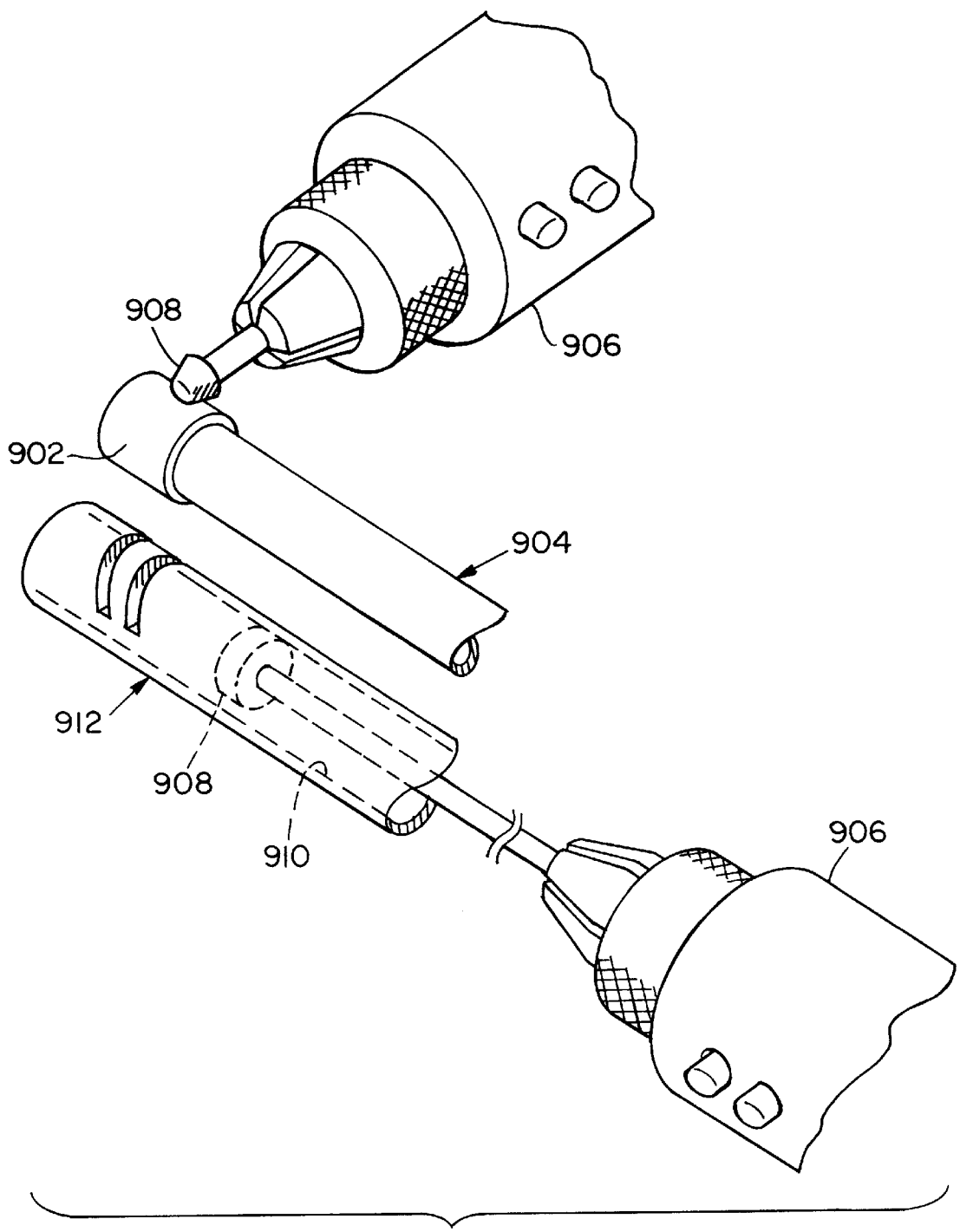
FIG. 8 is a graphical illustration showing the polishing of the concentric tubes.

FIG. 8 graphically illustrates a method of forming smooth sliding contact surfaces for the two concentric tubes of the present invention. In a preferred embodiment, the tubes are stainless steel, but they may be of other materials (such as composite materials) having similar properties and specifications. The outer surface 902 of the larger-diameter portion of the inner tube 904 is uniformly polished by a hand-held polishing drill 906 having a silver tip 908. The outer surface 902 is polished until the surface has a high luster and is uniformly smooth when examined under high magnification. The inner surface 910 of the outer tube 912 is similarly polished so that the two tubes fit snugly together with minimum friction.

Figure 11:
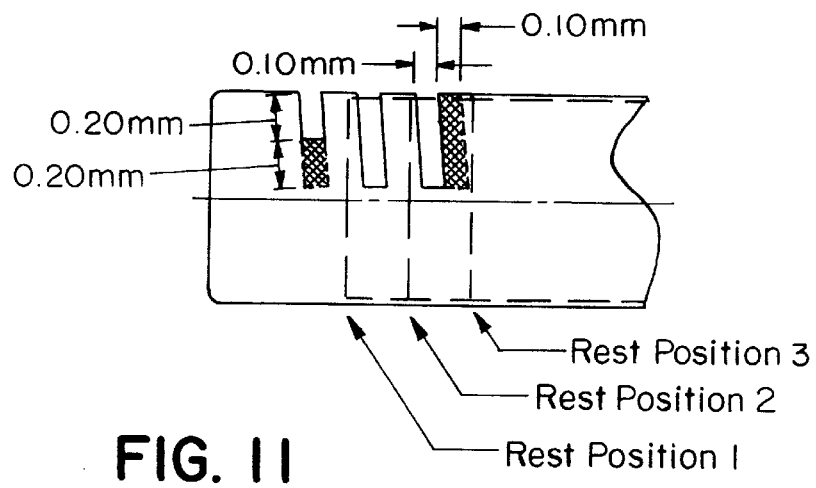
FIG. 11 shows an embodiment having three slits and shows the design ranges of the slit dimensions and selective stroke lengths.
Figure 12:
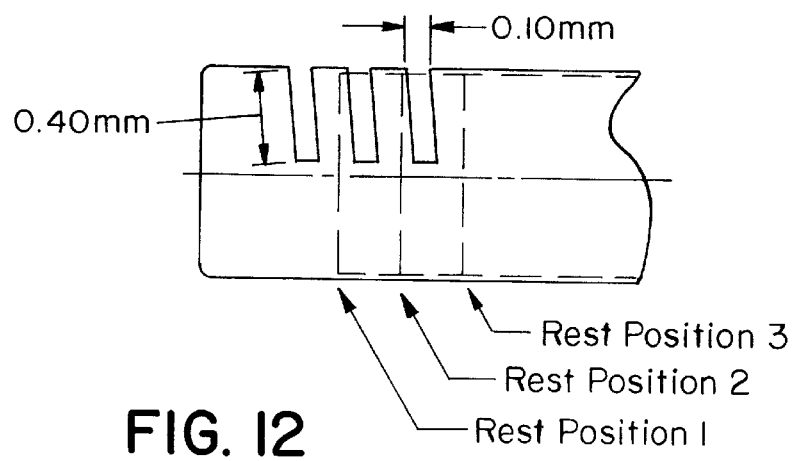
FIG. 12 illustrates three slits of the same dimensions with selective stroke lengths.
Figure 13:
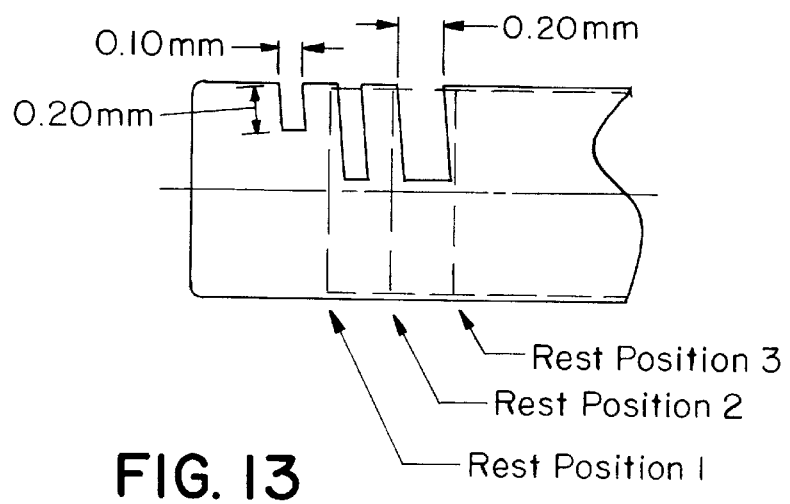
FIG. 13 illustrates the apparatus having slits of varying dimensions and selective stroke lengths.

The drive mechanism may include a selector 792 to reciprocate the inner tube through different selected stroke lengths past different sets of slits as illustrated in FIGS. 11, 12 and 13. The selector 792 may be an adjustable mechanical stop or it may adjust pneumatic control.

With reference to FIG. 12, the initial rest position of the cutter edge 206 may be at position 3 with the cutting stroke being toward the distal end from that position and the return stroke returning to that rest position. From that position, the cutting edge would pass all three slits illustrated in FIG. 12. However, for finer cutting action, the rest position may be reset to position two from which the cutting blade would reciprocate past only the two most distal slits. Finally, by setting the rest position at position one, the cutting edge would only reciprocate past the most distal slit for fine control of the shaving action.

FIGS. 11 and 13 also illustrate varying dimensions of the slits along the length of the outer tube. As illustrated in FIG. 11, the most distal slit may range in depth from 0.2 mm to 0.4 mm with a uniform width of 0.1 mm. The second slit from the distal end is preferably 0.4 mm deep-and 0.1 mm wide. The third slit from the distal end is preferably 0.4 mm deep but has a width within the range of 0.1 mm to 0.2 mm. The smaller depth of the first slit is intended to provide more fine control of the shaving action closest to the retina and when only one slit is active. The wider third slit allows for faster material removal during core vitrectomy. In the selective stroke approach, the third slit would only be active during core vitrectomy when the increased precision of the vitreous shaver is not so important. FIG. 13 illustrates the first slit at the shallowest end of the design range and the third slit at the widest of its design range.

EQUIVALENTS

Those skilled in the art will know, or be able to ascertain using no more than routine experimentation, many equivalents to the specific embodiments or the invention described herein. These and all other equivalents are intended to be encompassed by the following claims.

What is claimed is:

1. A vitreous removing apparatus for intraocular surgery comprising:

an outer tube having a port forming a closed distal end and at least one slit near the closed end for allowing vitreous tissue to flow into the outer tube, the slit having proximal and distal edges extending through a center between edge ends, each end of each edge being proximal relative to the respective center of the edge; and an inner tube concentric with the outer tube, snugly fitted inside the outer tube, having a sharp edge on a distal end for cutting vitreous tissue by sliding back and forth across the at least one slit, and being open at an end of the tube adjacent to the sharp edge to pass cut portions of vitreous tissue.

2. Apparatus as claimed in claim 1 comprising plural slits along the length of the outer tube.

3. Apparatus as claimed in claim 2 further comprising a selective drive mechanism for reciprocating the inner tube through different selected stroke lengths past different sets of slits.

4. Apparatus as claimed in claim 2 wherein the slits vary in dimensions from a lesser slit area at the distal end.

5. Apparatus as claimed in claim 4 having at least one slit which is deeper than the most distal slit.

6. Apparatus as claimed in claim 4 comprising at least one slit which is wider than the most distal slit.

7. Apparatus as claimed in claim 4 comprising at least one slit which is deeper and wider than the most distal slit.

8. A vitreous removing apparatus for intraocular surgery comprising:

an outer tube having a closed distal end and plural slits near the closed end for allowing vitreous tissue to flow into the outer tube, each slit baying proximal and distal edges extending through a center between edge ends each end of each edge being proximal relative to the respective center of the edge;

an inner tube concentric with the outer tube, snugly fitted inside the outer tube, having a sharp edge an a distal end for cutting vitreous tissue by sliding back and forth across the plural slits, and being open at an end of the tube adjacent to the sharp edge to pass cut portions of vitreous tissue; and a selective drive mechanism for reciprocating the inner tube through different selected stroke lengths past different sets of slits.

9. A vitreous removing apparatus for intraocular surgery comprising:

an outer tube having a closed distal end and plural slits near the closed end for allowing vitreous tissue to flow into the outer tube, the slits varying in dimensions from a lesser slit area at the distal end, each slit having proximal and distal edges extending through a center between edge end of each edge being proximal relative to the respective center of the edge; and an inner tube concentric with the outer tube, snugly fitted inside the outer tube, having a sharp edge on a distal end for cutting vitreous tissue by sliding back and forth across the plural slits, and being open at an end of the tube adjacent to the sharp edge to pass cut portions of vitreous tissue.

10. In intraocular surgery, a method of removing a vitreous base adherent to retinal surface by a vitreous cutting instrument comprising:

providing a vitreous cutting instrument comprising:

an outer tube having at least one slit near a closed distal end, each slit having a substantially uniform width angled at a significant angle from a plane perpendicular to the longitudinal axis of the outer tube, each slit having proximal and distal edges extending through a center between edge ends, each end of each edge being proximal relative to the respective center of the edge; and a slidable inner tube having a sharp cutting edge on a distal end and a driver and a vacuum coupled to a proximal end;

inserting the cutting instrument through an incision in the eye;

contacting the closed end of the cutting instrument on the retina surface by pushing the instrument through a layer of the vitreous base; and shaving the vitreous base from the retinal surface by moving the closed end of the cutting instrument along the retina while sliding the inner tube within the outer tube.

11. A method as claimed in claim 10 comprising plural slits along the length of the outer tube.

12. A method as claimed in claim 11 further comprising a selective drive mechanism for reciprocating the inner tube through different selected stroke lengths past different sets of slits.

13. A method as claimed in claim 11 wherein the slits vary in dimensions from a lesser slit area at the distal end.

14. In intraocular surgery, a method of removing a vitreous base adherent to retinal surface by a vitreous cutting instrument comprising:

providing a vitreous cutting instrument comprising:

an outer tube having plural slits near a closed distal end, each slit having proximal and distal edges extending through a center between edge ends, each end of each edge being proximal relative to the respective center of the edge; and a slidable inner tube having a sharp cutting edge on a distal end and a driver and a vacuum coupled to a proximal end;

inserting the cutting instrument through an incision in the eye;

contacting the closed end of the cutting instrument on the retinal surface by pushing the instrument through a layer of the vitreous base; and shaving the vitreous base from the retinal surface by moving the closed end of the cutting instrument along the retinal surface while reciprocating the inner tube within the outer tube, a drive mechanism for reciprocating the inner tube being selective to select different stroke lengths of the inner tube past different sets of slits.

15. In intraocular surgery, a method of removing a vitreous base adherent to retinal surface by a vitreous cutting instrument comprising:

providing a vitreous cutting instrument comprising:

an outer tube having plural slits near a closed distal end, the slits varying in dimensions from a lesser slit area at the distal end, each slit having proximal and distal edges extending through a center between edge ends, each end of each edge being proximal relative to the respective center of the edge; and a slidable inner tube having a sharp cutting edge on a distal end and a driver and a vacuum coupled to a proximal end;

inserting the cutting instrument through an incision in the eye;

contacting the closed end of the cutting instrument on the retinal surface by pushing the instrument through a layer of the vitreous base; and shaving the vitreous base from the retinal surface by moving the closed end of the cutting instrument along the retinal surface while reciprocating the inner tube within the outer tube.

* * * * *

UNITED STATES PATENT AND TRADEMARK OFFICE
CERTIFICATE OF CORRECTION

PATENT NO. : 5,843,111
DATED : December 1, 1998
INVENTOR(S) : Gerrit Jan Vijfvinkel It is certified that error appears in the above-identified patent and that said Letters Patent is hereby corrected as shown below:

Claim 8, column 7, line 5, delete "baying" and insert ---having---.
Claim 8, column 7, line 6, after "edge ends" insert ---,---.
Claim 9, column 7, line 26, after "between edge" insert ---ends, each---.

Signed and Sealed this

Twenty-seventh Day of April, 1999

Attest:

Q. TODD DICKINSON

*Attesting Officer*                *Acting Commissioner of Patents and Trademarks*

UNITED STATES PATENT AND TRADEMARK OFFICE
CERTIFICATE OF CORRECTION

PATENT NO. : 5,843,111
DATED : December 1, 1998
INVENTOR(S) : Gerrit Jan Vijfvinkel It is certified that error appears in the above-identified patent and that said Letters Patent is hereby corrected as shown below:

Cover page, Assignee, delete "Ophthalmic Research Center International bv" and insert ---Dutch Ophthalmic Research Center International bv---.

Signed and Sealed this

Fifth Day of October, 1999

Attest:

Q. TODD DICKINSON

*Attesting Officer*    *Acting Commissioner of Patents and Trademarks*